United States Patent [19]

Hommeltoft

[11] Patent Number: 5,396,017
[45] Date of Patent: Mar. 7, 1995

[54] ALKYLATION PROCESS

[75] Inventor: Sven I. Hommeltoft, Hillerod, Denmark

[73] Assignee: Haldor Topsoe A/S, Lyngby, Denmark

[21] Appl. No.: 142,203

[22] Filed: Oct. 25, 1993

Related U.S. Application Data

[63] Continuation-in-part of Ser. No. 142,801, Oct. 25, 1993.

[30] Foreign Application Priority Data

Aug. 5, 1993 [DK] Denmark .................... 0906/93

[51] Int. Cl.$^6$ ................................. C07C 2/62
[52] U.S. Cl. .................... 585/724; 585/725; 585/726
[58] Field of Search ............... 585/724, 725, 726

[56] References Cited

U.S. PATENT DOCUMENTS 5,306,859  4/1994  Eastman et al. .............. 585/724

FOREIGN PATENT DOCUMENTS 1183230  8/1986  Japan .

*Primary Examiner*—Asok Pal
*Attorney, Agent, or Firm*—Ostrolenk, Faber, Gerb & Soffen

[57] ABSTRACT

A process for the alkylation of hydrocarbon feedstock with an olefinic alkylating agent in the presence of a hydrogen fluoride catalyst, wherein the hydrogen fluoride catalyst is supported on a support material comprising a solid material with a Hammett acidity $H_0 > -8$ calculated on the material in protonated form.

6 Claims, No Drawings

ALKYLATION PROCESS

This is a continuation-in-part of application Ser. No. 08/142,801, which was filed on Oct. 25, 1993, now allowed.

BACKGROUND OF THE INVENTION

The present invention relates to improvements in the alkylation of aliphatic hydrocarbons in the presence of a hydrogen fluoride catalyst.

Acid catalyzed alkylation of aliphatic hydrocarbons with olefinic hydrocarbons is a well-known process for the preparation of high octane gasoline products. Alkylation of hydrocarbons is industrially accomplished in the liquid phase by mixing paraffins and olefins in the presence of a strong acid catalyst and stirring the mixture until the alkylation reaction was completed.

To date the usually employed acid catalysts for industrial alkylation of aliphatic hydrocarbons are concentrated sulphuric acid or anhydrous hydrofluoric acid, the strength of which may be increased by addition of a Lewis acid, such as $BF_3$ or $SbF_5$.

Those batch processes require large reaction volumes and thoroughly mixing of the alkylation mixture by mechanical mixing means in order to provide intimate contact between the acid catalyst, the reacting hydrocarbons and the olefinic alkylating agent.

Although being very efficient, a major drawback of the known alkylation processes are the environmental and health risk involved during handling of large amounts of the above acids, as necessary in the processes.

Besides being hazardous materials, sulphuric acid and hydrofluoric acid are aggressive compounds under the reaction conditions used in the alkylation processes. At ambient conditions hydrofluoric acid is a volatile gas, which necessitates the alkylation process to be carried out at low temperatures or at elevated pressure.

Increasing concerns about the safety of HF-alkylation have caused some improvements in the alkylation processes using this acid including modifications using additives and changes in reactor design (WO 93/00315, WO 93/00316, U.S. Pat. No. 5,196,627, U.S. Pat. No. 5,196,628, U.S. Pat. No. 5,196,629, U.S. Pat. No. 5,114,675 and U.S. Pat. No. 4,938,935). Though those measures lower the vapour pressure and thus lowers the risk slightly, they do not solve the problem involved in handling large quantities of liquid volatile hydrogen fluoride, which in case of an accident can escape to the environment.

DESCRIPTION OF THE INVENTION

We have found that the vapour pressure, and thus environmental or health risk, is reduced when using hydrogen fluoride during alkylation of hydrocarbons adsorbed on a solid material arranged in a suitable alkylation reactor without diminishing the acidity and the catalytic strength of the acid.

Based on the above findings, this invention provides a process for the alkylation of a hydrocarbon feedstock with an olefinic alkylating agent in the presence of a hydrogen fluoride catalyst, wherein the hydrogen fluoride catalyst being supported on a support material comprising a solid material with a Hammett acidity $H_0 > -8$ calculated on the material in protonated form.

The material may be any porous solid being able to form ionic adducts with the acid, and does not disintegrate under alkylation conditions. Such materials comprise polymer resins with pyridine groups, amine groups, other basic groups, or porous forms of carbon including forms of activated carbon. Presently, preferred materials are protonated forms of polyvinyl pyridine crosslinked with divinyl benzene and/or polystyrene amines.

The catalysts systems described above are applicable in most reactor configurations in which hydrocarbon feed is alkylated with an olefin including a fixed bed with moving catalyst band as mentioned in U.S. Pat. No. 5,220,095, the content of which is included herein by reference. Further suitable reaction systems include a fixed bed with acid recycle, various fluid bed configurations, stirred or in other ways agitated reactors and falling film reactors.

EXAMPLE 1

Poly-4-vinylpyridine support material crosslinked with divinyl benzene, commercially available under the trade name "Reillex 425 polymer", and having a particle size of 0.3–0.7 mm, was saturated with anhydrous HF by passing a stream of nitrogen through liquid HF and then through a bed of the support material until the material was saturated with HF. Excess HF was removed from the polyvinyl pyridine material by passing nitrogen through the bed at 50° C.

The HF-content in the saturated polymer was determined by tritiation to 52.6% (w/w).

A 100 ml reactor was packed with 81.26 g of the above HF-saturated material. 9.55 g HF was added to the reactor and a feed stream containing 5% (w/w) olefin in isobutane was pumped through the reactor, which was kept in a bath at 15°–40° C.

TABLE 1

| Feed: 5% (w/w) 2-butene in isobutane. | | |
|---|---|---|
| Temperature °C. | RON | MON |
| 40 | 94 | 92 |
| 30 | 94 | 92 |
| 25 | 95 | 93 |
| 20 | 96 | 94 |
| 15 | 96 | 94 |

EXAMPLE 2

Alkylation of a feed stream containing 2-butene and/or isobutene was carried out in a procedure similar to that described in Example 1. The results obtained with different feed streams at 20° C. are summarized in Table 2 below.

TABLE 2

| Feed mixture | RON | MON |
|---|---|---|
| 5% 2-butene in isobutane | 96 | 94 |
| 10% 2-butene in isobutane | 94 | 93 |
| 3% isobutene + 7% 2-butene in isobutane | 94 | 93 |
| 3% isobutene + 7% 2-butene in isobutane* | 94 | 93 |

*Extra 3.5 g trifluoromethanesulphonic acid added to the reactor.

I claim:

1. A process for the alkylation of hydrocarbon feedstock with an olefinic alkylating agent in the presence of a hydrogen fluoride catalyst, wherein the hydrogen fluoride catalyst is supported on a support material comprising a solid material with a Hammett acidity $H_0 > -8$ calculated on the material in protonated form.

2. The process of claim 1, wherein the support material comprises resins with basic groups being in their protonated form resistant against hydrogen fluoride.

3. The process of claim 2, wherein the basic groups comprise at least one of pyridines and/or amines.

4. The process of claim 2, wherein the resins comprise polyvinyl pyridine crosslinked with divinyl benzene.

5. The process of claim 2, wherein the resins comprise polystyrene amines.

6. The process of claim 1, wherein the hydrogen fluoride catalyst is arranged in a moveable reaction zone within a confined area of the support material.

* * * * *